United States Patent
Khan

(10) Patent No.: US 9,341,558 B1
(45) Date of Patent: May 17, 2016

(54) SYSTEM AND METHOD FOR MEASURING PERMEATION PROPERTIES OF CONCRETE AND POROUS MATERIALS

(71) Applicant: Mohammad Iqbal Khan, Riyadh (SA)

(72) Inventor: Mohammad Iqbal Khan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/835,666

(22) Filed: Aug. 25, 2015

(51) Int. Cl.
*G01N 15/08* (2006.01)

(52) U.S. Cl.
CPC ........ *G01N 15/0826* (2013.01); *G01N 15/0806* (2013.01)

(58) Field of Classification Search
CPC ... G01N 15/08; G01N 15/0806; G01N 33/38; G01N 33/383; G01N 33/388
USPC ............................................................ 73/38
See application file for complete search history.

(56) References Cited

U.S. PATENT DOCUMENTS

| | | | |
|---|---|---|---|
| 3,248,930 A | 5/1966 | Speegle et al. | |
| 3,934,455 A * | 1/1976 | Harrisberger | G01N 33/24 436/25 |
| 4,506,542 A * | 3/1985 | Rose | G01N 15/0826 73/38 |
| 4,895,450 A | 1/1990 | Holik | |
| 5,297,420 A * | 3/1994 | Gilliland | G01N 15/08 73/38 |
| 5,311,766 A * | 5/1994 | Persoff | G01N 15/0826 73/38 |
| 5,672,814 A * | 9/1997 | Doherty | G01N 33/24 73/38 |
| 5,679,885 A * | 10/1997 | Lenormand | G01N 15/0826 73/152.06 |
| 5,698,772 A * | 12/1997 | Deruyter | G01N 15/0826 73/152.07 |
| 6,055,850 A * | 5/2000 | Turner | G01N 33/24 73/38 |
| 6,321,589 B1 * | 11/2001 | Regimand | G01N 9/08 383/42 |
| 6,658,921 B2 | 12/2003 | Lavallée et al. | |
| 8,256,268 B2 * | 9/2012 | Khan | G01N 15/08 73/38 |
| 2013/0340505 A1 | 12/2013 | Go Boncan et al. | |

* cited by examiner

*Primary Examiner* — Daniel S Larkin
(74) *Attorney, Agent, or Firm* — Richard C. Litman

(57) ABSTRACT

The system for measuring permeation properties of concrete and porous materials includes a chamber having an upper plate, a lower plate, and a plurality of support members, the chamber being configured for holding a specimen. A plurality of supply tubes and a plurality of discharge tubes are in fluid communication with the chamber. A gas flow measurement assembly is in fluid communication with the chamber, the gas flow measurement assembly having a first pressure gauge and a gas flow meter. A water flow measurement assembly is in fluid communication with the chamber, the water flow measurement assembly having a second pressure gauge and a water flow meter. A gas cylinder is in fluid communication with the one of the plurality of supply tubes. The system may be used to measure gas permeability, water permeability, porosity, and absorption of concrete and other porous materials.

5 Claims, 3 Drawing Sheets

SYSTEM AND METHOD FOR MEASURING PERMEATION PROPERTIES OF CONCRETE AND POROUS MATERIALS

BACKGROUND OF THE INVENTION

1. Field of the Invention

The present invention relates to testing building materials, and particularly to a system and method for measuring permeation properties of concrete and porous materials.

2. Description of the Related Art

Typically, the permeability of concrete is one of the most critical parameters utilized in determining the durability of concrete in aggressive environments. As the permeability of concrete decreases, its durability performance, in terms of physico-chemical degradation, increases. Thus, permeation-related properties can significantly influence the strength and durability of concrete.

Although permeability normally refers to a pressure-induced flow, as in Darcy's Law of Permeability, the term permeability can encompass other types of flow. Permeability, absorption, and porosity are properties of concrete and other porous materials that typically govern the ingress of the aggressive substances into the material. Permeability is typically a measure of the ease with which the substances are transported into concrete due to a pressure differential, whereas absorption/porosity (saturation method) are measures of the absorption characteristics of concrete. Permeation, which can be dictated by the microstructure of concrete, controls the ingress of moisture, ionic, and gaseous species into concrete. Chemical degradation, such as corrosion of steel reinforcement, sulfate attack, carbonation, and alkali-aggregate reaction can result from a reaction between an external agent and the ingredients of concrete. Some physical effects, such as frost attack, can be greatly reduced by reducing the permeation of concrete. However, current systems and methods for determining the permeability of porous materials, such as concrete, are normally costly because of the set-up costs, the charges incurred due to the testing process, and space requirements, as well as being hazardous to the environment because of the chemicals, solvents, and regents that are required.

Thus, a system and method for measuring permeation properties of concrete and porous materials solving the aforementioned problems is desired.

SUMMARY OF THE INVENTION

The system for measuring permeation properties of concrete and porous materials includes a chamber having an upper plate, a lower plate, and a plurality of support members, the chamber being configured for holding a specimen. A plurality of supply tubes is positioned in fluid communication with the chamber, and a plurality of discharge tubes is positioned in fluid communication with the chamber. A gas flow measurement assembly is positioned in fluid communication with the chamber, the gas flow measurement assembly having a first pressure gauge and a gas flow meter. A water flow measurement assembly is positioned in fluid communication with the chamber, the water flow measurement assembly having a second pressure gauge and a water flow meter. Finally, a gas cylinder is positioned in fluid communication with the one of the plurality of supply tubes, the gas cylinder being configured for supplying pressurized gas into the chamber.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
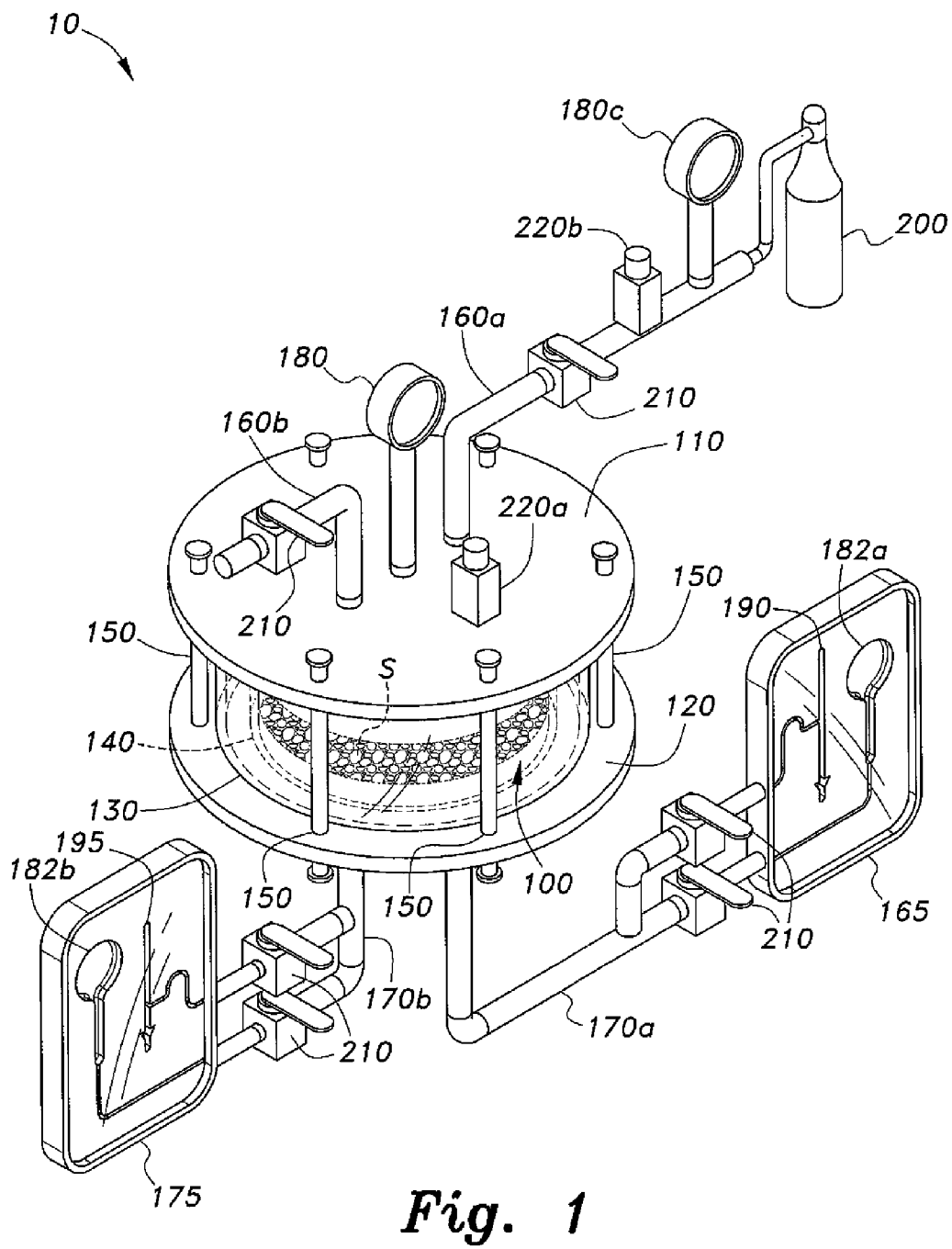
FIG. 1 is a perspective view of a system for measuring permeation properties of concrete and porous materials according to the present invention.
Figure 2:
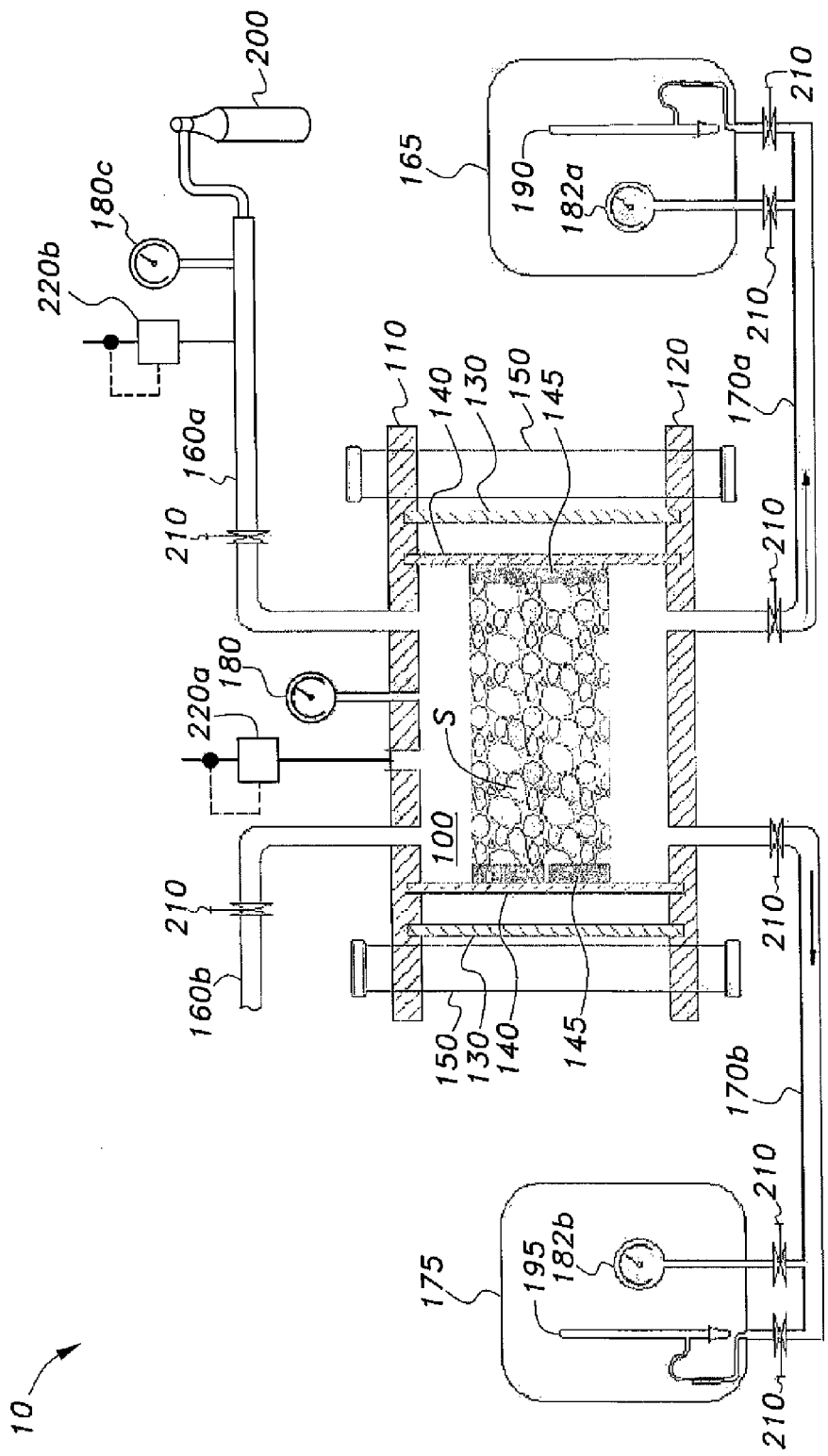
FIG. 2 is a schematic diagram of a system for measuring permeation properties of concrete and porous materials according to the present invention.

Referring to FIGS. 1 and 2, the system 10 for measuring permeation properties permeation properties of concrete and porous materials is capable of measuring permeation properties of all types of porous materials, including rocks, concrete (such as hardened, high-performance, normal-strength, high-strength, ultra-high strength, fiber-reinforced or dense concrete), and mortar. The system 10 includes a chamber 100 having an upper plate 110, a lower plate 120, and a plurality of support members 150 for supporting the upper plate 110 above the lower plate 120. The system 10 also includes a plurality of supply tubes, such as first supply tube 160a and second supply tube 160b, each supply tube 160a, 160b being disposed in fluid communication with the chamber 100. The system 10 further includes a plurality of discharge tubes, such as first discharge tube 170a and second discharge tube 170b, each discharge tube 170a, 170b being disposed in fluid communication with the chamber 100. The chamber 100 has an outer circumferential shell (wall) 130 and an inner circumferential shell (wall) 140 extending between the upper plate 110 and the lower plate 120 to define the chamber 100.

The system 10 also includes an air pressure gauge 180 disposed in fluid communication with the chamber 100. A gas flow measurement assembly 165 having a first pressure gauge 182a and a gas flow meter 190 is connected to the chamber 100, e.g., via discharge tube 170a. A water flow measurement assembly 175 having a second pressure gauge 182b and a water flow meter 195 is also connected to the chamber 100, e.g., via discharge tube 170b. A gas cylinder 200 is connected to the first supply tube 160a, the gas cylinder 200 being configured for supplying pressurized gas into the chamber 100. Since the pressure is applied by the gas cylinder 200, electricity is not needed to pressurize the gas, eliminating need for a pump. The first supply tube 160a includes a pressure gauge 180c configured for measuring pressure applied to the chamber 100 by the gas cylinder 200.

Having the first supply tube 160a configured for transferring a gas into the chamber 100 and the second supply tube 160b configured for transferring water into the chamber 100, as well as the corresponding gas flow measurement assembly 165 and the water flow measurement assembly 175, permits measurement of gas permeability, water permeability, absorption, and porosity of a single specimen S in the chamber 100, and can thereby eliminate variability among the four measurements. For the measurement of the specimen's S gas permeability, any suitable gas, such as oxygen or nitrogen, can be used. Since the system 10 uses commonly available gases, such as oxygen and nitrogen, and uses water, the system 10 is economical to use, and is environmentally friendly. Further, it is to be noted that other chemicals, reagents, and solvents are not required to test the specimen S.

The system 10 includes a plurality of valves 210 positioned in fluid communication with the chamber 100. Each of the valves 210 can be any type of suitable valve suitable for regulating the flow of gas and water, such as a check valve, a ball valve, or a diaphragm valve. The system 10 may include a first safety or pressure relief valve 220a positioned in fluid communication with the chamber 100 to prevent the pressure within the chamber 100 from reaching dangerous levels, and a second safety or pressure relief valve 220b positioned in fluid communication with the first supply tube 160a configured to prevent the pressure within the first supply tube 160a from reaching dangerous levels.

The chamber 100, the upper plate 110, the lower plate 120, and each of the plurality of support members 150 can be formed from any suitable material (such as metal) configured to hold a specimen S, such as a porous material or concrete having a strength grade in the range of 10 MPa to 120 MPa, for example, and receive pressurized gas and water through the first supply tube 160a and the second supply tube 160b, respectively. Further, the chamber 100 can have any suitable shape, such as a cylindrical shape, and any suitable dimensions capable of holding a specimen S having a diameter in the range of between 50 mm to 150 mm and a height of between 50 mm to 100 mm.

The outer shell 130 and the inner shell 140 can be formed from any suitable transparent material, such as glass, that can contain the pressurized gas and the water, while allowing people to see the effect of the pressurized gas and the water on the specimen S. Further, the inner shell 140 may have a sleeve 145 formed from any suitable material, such as rubber, to protect the inner shell 140 from being damaged by mixing the specimen S with the pressurized gas or water.

Each of the supply tubes 160a, 160b and each of the discharge tubes 170a, 170b can be formed from any suitable type of material, such as aluminum or polyvinyl chloride, to transfer pressurized gas and water into the chamber 100 holding the specimen S. Further, the air pressure gauge 180, as well as each pressure gauge 182a-182c, and each of the plurality of flow meters 190, 195 can be any suitable type of pressure gauge or flow meter, respectively, that can measure the gas permeability/air pressure index and water permeability/water pressure index, respectively. By exposing the specimen S to pressurized gas and water, the absorption and porosity properties of the specimen S can also be measured.

Normally the flow rate of fluid in porous materials, such as concrete or mortar, is low, thereby resulting in a laminar flow, instead of a turbulent flow. The laminar flow is dependent upon the properties of the fluid, namely viscosity and density, as well as the characteristics of the porous medium. When the pore system of the porous material, such as concrete, is fully saturated with liquid, such as water, then the water may flow through it if sufficient pressure is applied. The flow of non-compressible fluids (e.g., water) into a porous medium is governed Darcy's Law:

$$v = \frac{k}{\eta} \cdot \frac{dp}{dl},$$

where $v$ equals the flow rate (cm$^3$/s), $k$ equals the intrinsic permeability (m$^2$), $\eta$ equals the viscosity of the fluid (Ns/m$^2$), and dp/dl equals the pressure gradient in the direction flow.

The intrinsic permeability (k) has a unit of area and is dependent on the properties of the porous media only, since the viscosity of the fluid is included in this above-referenced equation, unlike the coefficient of permeability, which is a unit of velocity and is dependent on both properties of the fluid and of the porous media.

If gas flow rate (R) is the volume per second of the gas passing through the sample measured at an absolute pressure of $P_1$ (assuming an ideal gas), then:

$$k_g = \frac{2P_1 RL\eta}{A(P_2^2 - P_1^2)},$$

wherein $k_g$ equals the intrinsic permeability, L equals the thickness of specimen S (m), $P_2$ equals the absolute applied pressure (bars) (e.g., atmospheric pressure+pressure applied), $\eta$ equals the viscosity of oxygen (2.02×10$^5$ Ns/m$^2$ at 20° C.) and $P_1$ equals one atmosphere (e.g., 1 bar). To measure the specimen's gas permeability, the following equation can be used:

$$k_g = \frac{4.04RL \times 10^{-16}}{A(P_2^2 - P_1^2)}. \qquad (1)$$

The above equation can be used to estimate the oxygen permeability $k_g$ (m$^2$) for the given specimen.

Water permeability is the measurement of the passage of water through the specimen S, instead of gas. The governing equation for liquid (water) flowing through concrete under an applied pressure gradient for permeability of liquid is as follows:

$$k_w = \frac{RL\eta}{A(P_2^2 - P_1^2)},$$

wherein $k_w$ equals the water intrinsic permeability, L equals the thickness of the specimen S (m), $P_2$ equals the absolute applied pressure (bars) (e.g., atmospheric pressure+pressure applied), $\eta$ equals the viscosity of water (1.0×10$^3$ Ns/m$^2$ at 20° C.), and $P_1$ equals one atmosphere (e.g., 1 bar). To measure the specimen's water permeability, the following equation can be used:

$$k_w = \frac{RL \times 10^{-9}}{A(P_2 - P_1)}. \qquad (2)$$

The above equation can be used to estimate the water permeability $k_w$ (m$^2$) for the given specimen.

The porosity of porous materials, such as concrete, is the fraction of the bulk material volume of the material occupied by voids. While there are numerous techniques being employed for measuring porosity, the most commonly used techniques for paste, mortar, and other porous materials are helium pycnometry, mercury intrusion porosimetry (MIP), and the saturation method.

The saturation method is probably the best method, since it emulates the real situation encountered by concrete structures. To study the durability of concrete, it is necessary to know the maximum porosity that can be penetrated by water. One of the simplest ways to measure the porosity of porous materials, such as concrete, is by water absorption. The amount of water penetrating into the sample is a measure of the porosity and is calculated as follows:

$$Porosity = \frac{\text{Volume of voids}}{\text{Total volume}} \times 100, \text{ or}$$

$$P = \frac{W_{sat} - W_{oven}}{W_{sat} - W_{sub}} \times 100, \qquad (3)$$

wherein P equals the specimen's porosity (%), $W_{oven}$ equals the specimen's oven-dry weight, $W_{sat}$ equals the saturated surface dry weight, and $W_{sub}$ equals the specimen's saturated submerged weight.

Figure 3:
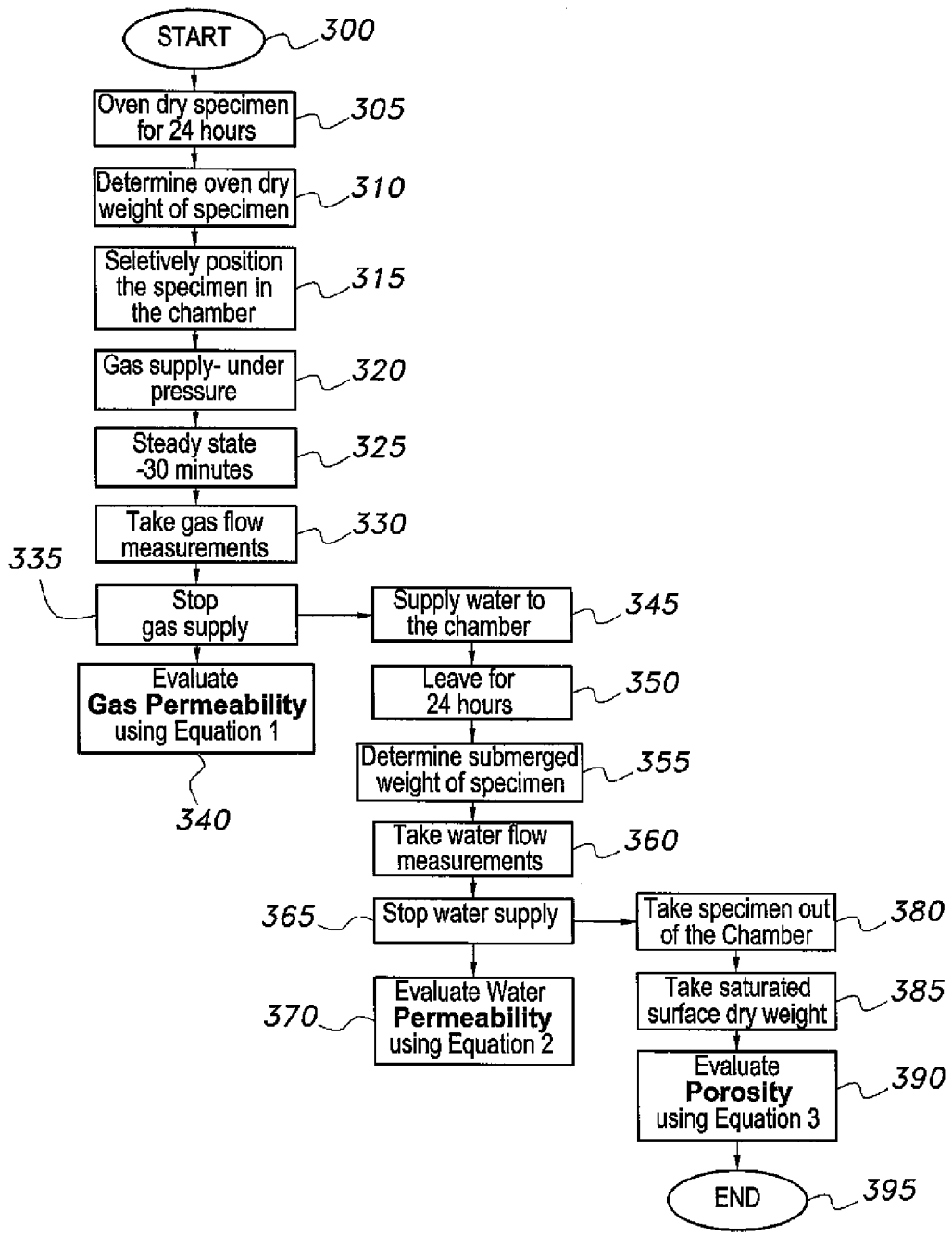
FIG. 3 is a flowchart of steps in a method for measuring permeation properties of concrete and porous materials according to the present invention.

FIG. 3 illustrates a method for measuring the permeation properties of concrete and other porous materials using the system 10 of FIGS. 1 and 2.

To begin testing the specimen S, at the Start 300, the specimen S should be dried, e.g., by drying in an oven for a predetermined amount of time (e.g., for twenty-four hours) (Step 305). Once the specimen S has been dried, the user can position the specimen S on a scale or other suitable means to determine the weight of the oven-dried specimen S (Step 310). The specimen S can then be selectively positioned inside the chamber 100 (Step 315), i.e., within the inner shell 140 of the chamber 100.

To determine the specimen's gas permeability, the valve 210 positioned on the second supply tube 160b and the valves 210 positioned on the second discharge tube 170b are closed to prevent the gas from escaping into the atmosphere through the second supply tube 160b and/or through the second discharge tube 170b. Further, each of the valves 210 positioned on the first discharge tube 170a is closed to allow the gas to fill the chamber 100 containing the specimen S. Once the necessary valves 210 have been closed, the user can activate the gas cylinder 200 (i.e., open the valve 210 in the first supply tube 160a) to introduce pressurized gas inside the chamber 100, preferably maintaining a constant pressure (Step 320). For example, the gas can flow from the gas cylinder 200 through the first supply tube 160a and into the chamber 100. After the chamber 100 has been filled with gas and a predetermined amount of pressure has been reached within the chamber 100, the valve 210 positioned on the first supply tube 160a is closed to prevent any more gas from entering the chamber 100. Further, the pressure relief valve 220b positioned on the first supply tube 160a may open to prevent the unnecessary build-up of pressure that can cause the first supply tube 160a to rupture. The specimen S can then be exposed to the pressurized gas for a predetermined amount of time, such as approximately thirty minutes, until the specimen S reaches a steady state (Step 325).

After the predetermined amount of time, such as approximately thirty minutes, has lapsed, the valves 210 positioned on the first discharge tube 170a are opened to create a vacuum to draw the gas through the specimen S and through the first discharge tube 170a and into the first pressure gauge 182a and into the gas flow meter 190, respectively, positioned in the gas flow measurement assembly 165. The gas pressure and the flow of gas can then be measured by the first pressure gauge 182a and the gas flow meter 190 (Step 330). After the gas flow measurements are taken, the gas can be shut off (Step 335).

The user can then utilize the measurement in equation (1) (described above) to evaluate the gas permeability of the specimen S (Step 340).

To determine the specimen's S water permeability, the valve 210 positioned on the first supply tube 160a, as well as the valves 210 positioned on the first discharge tube 170a, are closed to prevent water from escaping through the first supply tube 160a and/or through the first discharge tube 170a. Further, the valves 210 positioned on the second discharge tube 170b are closed to allow water to remain in the chamber 100. Once the necessary valves 210 have been closed, the user can activate a water supply to supply water through the second supply tube 170b into the chamber 100 having the specimen S (Step 345).

Once the water has been supplied into the chamber 100 holding the specimen S, the specimen S is left in the water for a predetermined amount of time, e.g., twenty-four hours (Step 350). Allowing the specimen S to remain submerged at a constant pressure for approximately twenty-four hours allows the water to enter each of the various pores in the specimen S. After the predetermined amount of time, the submerged weight of the specimen S can be determined (Step 355) by measuring the amount of water that has been displaced. After determining the submerged weight of the specimen S, the user can open the valves 210 positioned on the second discharge tube 170b to create a vacuum so that the water can flow through the specimen S and, in turn, through the second discharge tube 170b and into the second pressure gauge 182b and into the water flow meter 195, respectively, positioned in the water flow measurement assembly 175.

The pressure gradient created between the water remaining above the specimen S and the water beneath the specimen S can create sufficient pressure for the water to flow through the specimen S. The water pressure and the flow of water can subsequently be measured by the second pressure gauge 182b and the water flow meter 195, respectively, positioned in the water flow measurement assembly 175 (Step 360). After the measurements have been taken, the water supply can be turned off (Step 365). The measurements can subsequently be used with equation (2) (described above) to evaluate the water permeability of the specimen S (Step 370). By removing the gas from the chamber 100, the pores in the concrete, for example, can open and allow for water to penetrate to determine the specimen's S water permeability.

To determine the specimen's S porosity, the user can remove the specimen from the chamber 100 (Step 380). Once the specimen S has been removed, the user can take the specimen's S saturated surface dry weight (Step 385). Subsequently, the user can use the oven-dry weight, determined in Step 310, as well as the submerged weight, determined in Step 355, and the saturated, surface dry weight, determined in Step 385, in equation (3) (discussed above) to evaluate the porosity of the specimen S (Step 390). Once the porosity has been determined, the method is compete (Step 395). The user can then compare the gas permeability, the water permeability, and the porosity of the specimen S to that of other types of porous material to determine which is the best material.

After the gas permeability, water permeability, porosity, and absorption measurements have been taken, the same specimen S can be used to conduct a chloride penetration test in accordance with ASTM C1202. For best results when conducting a chloride permeability test using the system 10, the specimen should have a diameter measuring 100 mm and a height measuring 50 mm. Further, it is to be noted that the system 10 can be used to measure any individual characteristic at any given time without having to measure the other properties.

It should be noted that this Project was funded by the National Plan for Science, Technology and Innovation (MAARIFAH), King Abdulaziz City for Science and Technology, Kingdom of Saudi Arabia, Award Number 14-BUI2262-02.

It is to be understood that the present invention is not limited to the embodiments described above, but encompasses any and all embodiments within the scope of the following claims.

I claim:

1. A system for measuring permeation properties of concrete and porous materials, consisting of:
    a chamber having an upper plate, a lower plate, a plurality of support members separating the upper plate and the lower plate, and at least one circumferential wall extending between the upper plate and the lower plate, wherein the at least one circumferential wall comprises an inner shell and an outer shell, the chamber being configured for holding a specimen;
    a plurality of supply tubes connected in fluid communication with the chamber, wherein the supply tubes consist of a single gas supply tube and a single liquid supply tube;
    a plurality of discharge tubes connected in fluid communication with the chamber, wherein the discharge tubes consist of a single gas discharge tube and a single liquid discharge tube;
    a gas flow measurement assembly connected in fluid communication with the gas discharge tube, the gas flow measurement assembly having a first pressure gauge and a gas flow meter;
    a liquid flow measurement assembly connected in fluid communication with the liquid discharge tube, the water flow measurement assembly having a second pressure gauge and a water flow meter;
    a gas cylinder connected in fluid communication with the gas supply tube, the gas cylinder being configured for supplying pressurized gas into the chamber;
    a plurality of valves disposed in the supply tubes and in the discharge tubes for regulating the flow of gas and liquid through the system;
    an air pressure gauge in fluid communication with the chamber;
    a first pressure relief valve in fluid communication with the chamber; and
    a second pressure relief valve in fluid communication with the gas supply tube.

2. The system for measuring permeation properties according to claim 1, wherein said valves comprise valves selected from the group consisting of check valves, ball valves, and diaphragm valves.

3. A method for measuring permeation properties of concrete and porous materials comprising the steps of:
    (a) providing a system for measuring permeation properties of concrete and porous materials according to claim 1;
    (b) drying the specimen for a predetermined amount of time to form a dried specimen;
    (c) determining the weight of the dried specimen;
    (d) selectively positioning the specimen in the chamber;
    (e) selectively applying pressurized gas into the chamber holding the specimen; and
    (f) determining the gas permeability of the dried specimen.

4. The method for measuring permeation properties of concrete and porous materials according to claim 3, further comprising the steps of:
    (a) selectively supplying water into the chamber holding the specimen;
    (b) leaving the specimen in the water for a predetermined amount of time;
    (c) determining the submerged weight of the specimen; and
    (d) determining the water permeability of the specimen.

5. The method for measuring permeation properties of concrete and porous materials according to claim 4, further comprising the steps of:
    (a) removing the specimen from the chamber;
    (b) determining the saturated, surface dry weight of the specimen; and
    (c) determining the porosity of the specimen.

* * * * *